United States Patent
Zhang et al.

(10) Patent No.: US 7,327,830 B2
(45) Date of Patent: Feb. 5, 2008

(54) COLLIMATION AND CALIBRATION INTEGRATIVE APPARATUS FOR CONTAINER INSPECTION SYSTEM

(75) Inventors: Fengjun Zhang, Beijing (CN); Shangmin Sun, Beijing (CN); Junli Li, Beijing (CN); Yanli Deng, Beijing (CN); Zhizhong Liang, Beijing (CN); Yanjun Han, Beijing (CN); Guibin Lin, Beijing (CN); Bing Wang, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 35 days.

(21) Appl. No.: 11/490,722

(22) Filed: Jul. 21, 2006

(65) Prior Publication Data
US 2007/0019786 A1    Jan. 25, 2007

(30) Foreign Application Priority Data
Jul. 22, 2005    (CN)    ................. 2005 1 0012249

(51) Int. Cl.
*G21K 1/02*    (2006.01)
*G01D 18/00*    (2006.01)
*G01N 23/04*    (2006.01)

(52) U.S. Cl. ...................... 378/147; 378/207
(58) Field of Classification Search ............... 378/147, 378/207
See application file for complete search history.

(56) References Cited

U.S. PATENT DOCUMENTS

| | | | | |
|---|---|---|---|---|
| 2,469,206 A | * | 5/1949 | Rich | 378/53 |
| 3,206,604 A | * | 9/1965 | Burchell | 378/153 |
| 3,543,027 A | * | 11/1970 | Nickless et al. | 250/363.01 |
| 3,631,249 A | * | 12/1971 | Friede et al. | 378/157 |
| 3,894,234 A | * | 7/1975 | Mauch et al. | 378/146 |
| 5,287,396 A | * | 2/1994 | Stegehuis | 378/98.2 |
| 6,307,918 B1 | * | 10/2001 | Toth et al. | 378/158 |
| 2007/0018117 A1 | * | 1/2007 | Calderon et al. | 250/492.1 |

\* cited by examiner

*Primary Examiner*—Edward J. Glick
*Assistant Examiner*—Thomas R. Artman
(74) *Attorney, Agent, or Firm*—Osha Liang LLP

(57) ABSTRACT

A collimation and calibration integrative apparatus for container inspection system includes a collimating block; a calibrating block; a base plate; a motor and a plurality of supporting units fixed on the base plate; a transmission unit coupled to the motor for transmitting movement from the motor to a bearing plate, characterized in that the apparatus further includes: a sliding plate having one end connected to the bearing plate and the other end slidably fitted to guide rails provided on the base plate; a stationary plate fixedly connected to the sliding plate, wherein the collimating block and the calibrating block are provided on the stationary plate to form an integrative structure and an assembly gap is formed between the collimating block and the calibrating block, whereby the collimating block and the calibrating block on the stationary plate are driven by the transmission unit and the bearing plate to be moved integrally.

26 Claims, 1 Drawing Sheet

COLLIMATION AND CALIBRATION INTEGRATIVE APPARATUS FOR CONTAINER INSPECTION SYSTEM

BACKGROUND OF THE INVENTION

1. Field of the Invention

The present invention relates to technique of inspection by radiation scanning and imaging, in particularly, to a collimation and calibration integrative apparatus for container inspection system.

2. Description of the Related Art

A radiation source for generating high energy X-rays and a detector array for receiving the X-rays penetrating through a container are key elements for a container inspection system. When a container is penetrated by X-rays, the penetrated X-rays are transmitted to the detector. The density distribution of the objects in the container is reflected by the strength variation of the penetrated X-rays, and is then obtained by converting the strength of the penetrated X-rays into a gray scale of an image. At present, the conventional container inspection system is classified into such types as stationary container inspection system, mobile container inspection system, relocatable container inspection system, and so on. In the above container inspection systems, X-rays emitted from the radiation source are required to be calibrated and collimated. In the prior art, a calibrator and a collimator are separate units and arranged in turn in front of the radiation source. Thus, when in use, the position and angle of the calibrator and the collimator are required to be adjusted separately. The two units occupy large spaces in the system and are very heavy. In particular, for a relocatable container inspection system which generally uses a linear electron accelerator mounted in a compartment, it is very difficult to use the conventional calibrator and collimator because the inner space of the compartment should be as small as possible. The installation and adjustment are also very inconvenient.

SUMMARY OF INVENTION

In view of the above disadvantages in the prior art, it is an object of the present invention to provide a collimation and Calibration integrative apparatus for container inspection system. In the present invention, a calibrating block performs a calibration function when the apparatus is used for calibration function, and the calibrating block and a collimating block form a collimator to perform a collimation function when the apparatus is used in a regular inspection function. The collimation and calibration integrative apparatus according to the present invention has a small size and a reduced weight, it is also easy to install and convenient for operation.

In order to achieve one or more aspects of the above object, the present invention provides the following technical schemes:

A collimation and calibration integrative apparatus for container inspection system, comprising a collimating block; a calibrating block; a base plate; a motor and a plurality of supporting units which are fixed on the base plate; a transmission unit coupled to an output end of the motor for transmitting a movement of the motor to a bearing plate, characterized in that the apparatus further comprises:

a sliding plate having one end connected to the bearing plate and the other end slidably fitted to guide rails provided on the base plate;

a stationary plate provided on and fixedly connected to the sliding plate, wherein, the collimating block and the calibrating block are mounted on the stationary plate to form an integrative structure and an assembly gap is formed between the collimating block and the calibrating block, thereby the collimating block and the calibrating block on the stationary plate are driven by the transmission unit and the bearing plate to be moved integrally.

In the above integrative apparatus, the assembly gap is a collimating slit having a uniform width.

Preferably, the transmission unit comprises: a screw rod coupled to the output end of the motor and supported by the plurality of bearing blocks; a screw nut screw-engaged with the screw rod; and a connecting plate fixedly connected to the bearing plate.

Preferably, in the above integrative apparatus, the bearing block is provided with a rolling bearing or a sliding bearing therein.

Preferably, in the above integrative apparatus, a channel steel for reinforcement and height adjustment is provided between the base plate and the guide rails.

Preferably, in the above integrative apparatus, the sectional inner contour of the sliding plate matches with the sectional outer contour of the guide rails, and they slidably fit with each other with an allowable clearance therebetween.

Preferably, in the above integrative apparatus, there are two sliding plates which are provided at the ends on both sides of the bearing plate respectively.

Preferably, in the above integrative apparatus, the connecting plate is connected to a middle part of the bearing plate.

Preferably, in the above integrative apparatus, the motor is a servo motor or stepper motor.

With the above structure of the present invention, the collimating block and the calibrating block are integrally formed on the stationary plate, by which the size of the apparatus is reduced compared with the conventional one having two separate units. The stationary plate is controlled by the motor to move therewith, thus meeting the technical requirements of the inspecting system for calibration and collimation. Compared with the prior art, the present invention can save installation space and reduce the weight of the apparatus. When in use, the calibrating block performs a calibration function and a central gap formed between the collimation block and the calibrating block performs a X-ray collimation function. The adjustment and control of the whole apparatus is more convenient.

BRIEF DESCRIPTION OF THE DRAWINGS

The present invention will be described in detail with reference to the attached drawings and embodiments, wherein.

DETAILED DESCRIPTION OF THE PREFERRED EMBODIMENTS

Embodiments of the present invention will be described in detail with reference to attached drawings. It should be noted that the embodiments are only for the illustrative purpose, not intent to limit the scope of the present invention.

Figure 1:
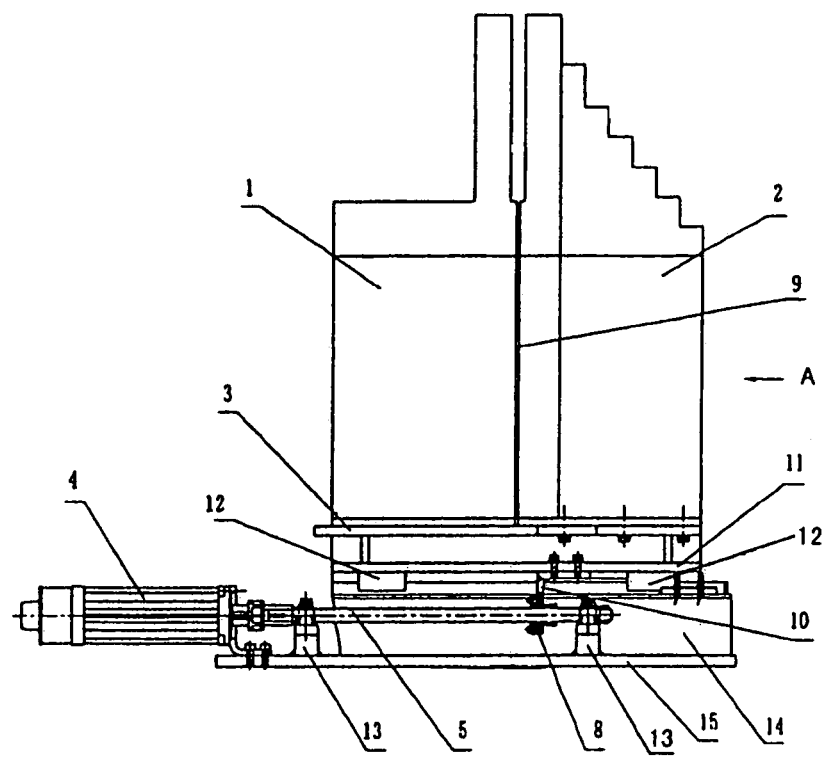
FIG. 1 is a schematic view showing the structure of the present invention.
Figure 2:
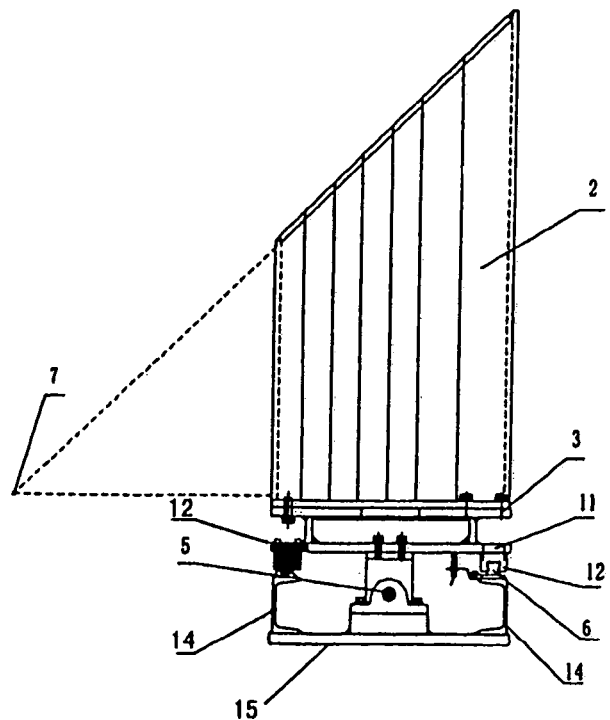
FIG. 2 is a schematic view showing the state in use of the apparatus in FIG. 1 in the direction of A.

As shown in FIG. 1, the apparatus of the present invention comprises a collimating block 1, a calibrating block 2, a motor 4 such as a servo motor, a screw rod 5 which is coupled to an output end of the servo motor 4 and is supported by two bearing blocks 13 provided with a rolling bearing or a sliding bearing therein. The motor 4 and each bearing block 13 are fixed on a base plate 15, and the screw rod 5 is mounted with a nut 8 matched therewith. The collimating block 1 and the calibrating block 2 are formed with an assembly gap therebetween and provided on a stationary plate 3 to form an integrative structure. The assembly gap between the collimating block 1 and the calibrating block 2 is a collimating slit 9 having a uniform width. A bearing plate 11 is provided under the stationary plate 3, the bearing plate 1 provided with a sliding plate 12 at each side thereof and with a connecting plate 10 at a middle part thereof. The sliding plate 12 is disposed on guide rails 6 provided at both sides of the base plate 15. The sectional inner contour of the sliding plate 12 matches with the sectional outer contour of the guide rails 6, and they slidably fit with each other with a clearance fit therebetween. A channel steel 14 for reinforcement and height adjustment may be provided between the base plate 15 and the guide rails 6. The connecting plate 10 is fixed to the nut 8. When the motor 4 is enabled, the rotary movement of the screw rod 5 drives the nuts to move linearly, thereby the collimating block 1 and the calibrating block 2 on the stationary plate 3 are moved integrally. It is apparent for a person skilled in the art that other transmission units also can be used in the present invention to transmit the rotary movement from the motor 4 to the connecting plate 10, without being limited to the transmission by screw rod 5 and the nut 8. Also, the servo motor can be replaced by a stepper motor.

When the present invention is applied to a movable container inspection system to inspect a container, the motor 4 is enabled to drive the screw rod 5 to rotate. The sliding plate 12 mounted under the bearing plate 11 is driven to move in a fore-and-aft direction through the screw rod 5 and the nut 8, thereby the collimating block 1 and the calibrating block 2 on the stationary plate 3 are moved integrally. The calibrating block 2 calibrates data when a calibration function is performed on the system. When the system is used to inspect a container, X-rays emitted from a radiation source 7 are in alignment with the collimating slit 9 between the collimating block 1 and the calibrating block 2, thus the calibrating block 1 and a collimating block 2 form a collimator, allowing the X-rays to pass through the collimating slit 9 to scan the container.

Although several preferred embodiments have been shown and described, it would be appreciated by a person skilled in the art that changes can be made to the present invention without departing from its substantial spirit or essential characteristics. All the changes occurring within the scope of this invention or within the equivalent scope are included in this invention.

What is claimed is:

1. A collimation and calibration integrative apparatus for container inspection system, comprising:
   a collimating block; a calibrating block; a base plate; a motor and a plurality of bearing blocks which are fixed on the base plate; a transmission unit coupled to an output end of the motor for transmitting a movement of the motor to a bearing plate, characterized in that the apparatus further comprises:
   a sliding plate having one end connected to the bearing plate and the other end slidably fitted to guide rails provided on the base plate;
   a stationary plate provided on and fixedly connected to the sliding plate, wherein, the collimating block and the calibrating block are mounted on the stationary plate to form an integrative structure and an assembly gap is formed between the collimating block and the calibrating block, thereby the collimating block and the calibrating block on the stationary plate are driven by the transmission unit and the bearing plate to be moved integrally.

2. The collimation and calibration integrative apparatus for container inspection system according to claim 1, characterized in that:
   the assembly gap is a collimating slit having a uniform width.

3. The collimation and calibration integrative apparatus for container inspection system according to claim 1, characterized in that the transmission unit comprises:
   a screw rod coupled to the output end of the motor and supported by the plurality of bearing blocks;
   a screw nut screw-engaged with the screw rod; and a connecting plate fixedly connected to the bearing plate.

4. The collimation and calibration integrative apparatus for container inspection system according to claim 1, characterized in that:
   a channel steel for reinforcement and height adjustment is provided between the base plate and the guide rails.

5. The collimation and calibration integrative apparatus for container inspection system according to claim 1, characterized in that:
   the sectional inner contour of the sliding plate matches with the sectional outer contour of the guide rails, and they slidably fit with each other with an allowable clearance therebetween.

6. The collimation and calibration integrative apparatus for container inspection system according to claim 1, characterized in that:
   there are two sliding plates which are provided at the ends on both sides of the bearing plate respectively.

7. The collimation and calibration integrative apparatus for container inspection system according to claim 3, characterized in that:
   the connecting plate is connected to a middle part of the bearing plate.

8. The collimation and calibration integrative apparatus for container inspection system according to claim 1, characterized in that:
   the motor is a servo motor or stepper motor.

9. The collimation and calibration integrative apparatus for container inspection system according to claim 6, characterized in that:
   a channel steel for reinforcement and height adjustment is provided between the base plate and the guide rails.

10. The collimation and calibration integrative apparatus for container inspection system according to claim 6, characterized in that:
    the sectional inner contour of the sliding plate matches with the sectional outer contour of the guide rails, and they slidably fit with each other with an allowable clearance therebetween.

11. The collimation and calibration integrative apparatus for container inspection system according to claim 1, characterized in that:
    the bearing block is provided with a rolling bearing therein.

12. The collimation and calibration integrative apparatus for container inspection system according to claim 1, characterized in that:

the bearing block is provided with a sliding bearing therein.

13. The collimation and calibration integrative apparatus for container inspection system according to claim 6, characterized in that:

the motor is a servo motor or stepper motor.

14. The collimation and calibration integrative apparatus for container inspection system according to claim 6, characterized in that:

the bearing block is provided with a rolling bearing or a sliding bearing therein.

15. The collimation and calibration integrative apparatus for container inspection system according to claim 2, characterized in that:

a channel steel for reinforcement and height adjustment is provided between the base plate and the guide rails.

16. The collimation and calibration integrative apparatus for container inspection system according to claim 3, characterized in that:

a channel steel for reinforcement and height adjustment is provided between the base plate and the guide rails.

17. The collimation and calibration integrative apparatus for container inspection system according to claim 2, characterized in that:

the sectional inner contour of the sliding plate matches with the sectional outer contour of the guide rails, and they slidably fit with each other with an allowable clearance therebetween.

18. The collimation and calibration integrative apparatus for container inspection system according to claim 3, characterized in that:

the sectional inner contour of the sliding plate matches with the sectional outer contour of the guide rails, and they slidably fit with each other with an allowable clearance therebetween.

19. The collimation and calibration integrative apparatus for container inspection system according to claim 2, characterized in that:

the motor is a servo motor or stepper motor.

20. The collimation and calibration integrative apparatus for container inspection system according to claim 3, characterized in that:

the motor is a servo motor or stepper motor.

21. The collimation and calibration integrative apparatus for container inspection system according to claim 7, characterized in that:

a channel steel for reinforcement and height adjustment is provided between the base plate and the guide rails.

22. The collimation and calibration integrative apparatus for container inspection system according to claim 7, characterized in that:

the sectional inner contour of the sliding plate matches with the sectional outer contour of the guide rails, and they slidably fit with each other with an allowable clearance therebetween.

23. The collimation and calibration integrative apparatus for container inspection system according to claim 2, characterized in that:

the bearing block is provided with a rolling bearing or a sliding bearing therein.

24. The collimation and calibration integrative apparatus for container inspection system according to claim 3, characterized in that:

the bearing block is provided with a rolling bearing or a sliding bearing therein.

25. The collimation and calibration integrative apparatus for container inspection system according to claim 7, characterized in that:

the motor is a servo motor or stepper motor.

26. The collimation and calibration integrative apparatus for container inspection system according to claim 7, characterized in that:

the bearing block is provided with a rolling bearing or a sliding bearing therein.

\* \* \* \* \*